United States Patent [19]

Snoeyenbos et al.

[11] 4,335,107

[45] Jun. 15, 1982

[54] MIXTURE TO PROTECT POULTRY FROM SALMONELLA

[76] Inventors: Glenn H. Snoeyenbos, 42 Hills Rd., Amherst, Mass. 01002; Olga M. Weinack, 179 Woodbridge St., South Hadley, Mass. 01075; Charles F. Smyser, 49 Harlow Dr., Amherst, Mass. 01002

[21] Appl. No.: 912,829

[22] Filed: Jun. 5, 1978

[51] Int. Cl.³ .................. A61K 35/12; A61K 35/66; A61K 35/74; A61K 39/295
[52] U.S. Cl. .................................. 424/93; 426/61; 426/71
[58] Field of Search .................. 424/88–93; 426/61–71

[56] References Cited

U.S. PATENT DOCUMENTS

| | | | |
|---|---|---|---|
| 3,072,528 | 1/1963 | Kludas et al. | 424/93 |
| 3,369,969 | 2/1968 | Nouvel | 424/93 |
| 3,713,836 | 1/1973 | Carlsson | 426/61 |
| 3,875,306 | 4/1975 | Alstrom | 426/61 |
| 3,940,491 | 2/1976 | Crutcher et al. | 426/2 |
| 3,984,575 | 10/1976 | Farr | 426/61 |

FOREIGN PATENT DOCUMENTS

| | | | |
|---|---|---|---|
| 532242 | 10/1956 | Canada | 426/71 |
| 1812903 | 8/1970 | Fed. Rep. of Germany | 424/93 |
| 2134179 | 1/1973 | Fed. Rep. of Germany | 424/93 |
| 1275M | 5/1962 | France | 424/93 |
| 3233M | 4/1965 | France | 424/93 |
| 2096887 | 3/1972 | France | 424/93 |
| 46-15643 | 4/1971 | Japan | 424/93 |
| 49-47831 | 12/1974 | Japan | 426/61 |
| 51-106725 | 9/1976 | Japan | 426/61 |
| 51-106726 | 9/1976 | Japan | 424/93 |
| 930107 | 7/1963 | United Kingdom | 424/93 |

OTHER PUBLICATIONS

Proceedings, National Salmonellosis Seminar, Jan. 10–11, 1978, citing: Williams, Research Contributions to Salmonellosis Prevention and Control (9 pages), Pomeroy et al., Salmonellosis Prevention and Control at the Producer Level in Turkeys, (15 pages) and Snoeyenbos, Prevention and Control of Salmonellosis in Chickens at the Producer Level.
Webster's New International Dictionary of the English Language, Unabridged G and C Nerriam Co., Springfield, Mass. (1963), p. 503, "coprophagy".
The Oxford English Dictionary, vol. 11C, (1933), p. 976, "coprophagist".
Snoeyenbas, G. H. et al., Avian Dis 22(2): 273–287, Jun. 1978, Protecting Chicks and Poulets From Salmonellae by Oral Administration of "Normal" Gut Microflora.
Bowman, P. J. et al., Proc. 1st A'Asian Poultry and Stock Feed Convention Melbourne, Australia, pp. 318–319, (1976), Further Studies on Competitive Exclusion in Controlling Salmonella Infections in Young Chicks.
Hughes, K. L., Australian Vet. J. 48: 508–514, (1972), Recent Knowledge of the Strict Anaerobes of the Gut.
Idsiak, E. S. et al., International Symposium on Salmonella and Prospects for Control, Univ. Guelph, Ontario, Canada, Jun. 8–11, 1977, The Influence of Normal Intestinal Flora of Chicks on *S. infantis* and *S. Typhimurium*.
Lloyd, A. B. et al., Australian Vet. J. 53: 82–87, (1977), Prevention of Salmonella Typhimurium Infection in Poultry by Pretreatment of Chicks and Poults with Intestinal Extracts.
Nurmi, E. et al., Nature, 241: 210–211, (1973), New Aspects of Salmonella Infection in Broiler Production.
Rantala, M. et al., Br. Poult. Sci. 14: 627–630, (1973), Prevention of the Growth of Salmonella Infantis in Chicks by the Flora of the Alimentary Tract of Chickens.
Rigby, C. et al., Proc. Int. Sympos. Salmonella and Prospects for Control, Univ. Guelph, Ontario, Canada, Jun. 8–11, 1977, The Effect of Normal Intestinal Flora on the Salmonella Carrier State in Poultry (*S. Thompson* and *S. Typhimurium*).
Panda, B. et al., Indian Poult. Rev. 8(12): 21–23 Feb. 1977, Alternate Feeds for Poultry-Dried Poultry Manure.
Kirilov, M. P. et al., Sov. Agric. Sci. 11: 46–48, 1976, Nitrogen Metabolism in Cattle Fed with Bulk Feeds Containing Dry Poultry Manure.
Denisov, N. et al., Zhivotnovodstvo 12: 43–45, Dec. 1975, Addition of Poultry Manure to Mixed Feeds.
Denisovni et al., Zhivotnovodstvo 2:45–47, Feb. 1973, Processed Poultry Manure for Use in Mixed Feeds.
Waldroup, P. W. et al., Arkansas Farmres, 23(3): 10 Jun. 74, Dried Poultry Manure in Laying Hen Feeds.
Waldroup, P. W., et al., Feed Ind. 50(3): 10,12, 1974, Dried Poultry Manure in Laying Hen Feeds.
Chillar, K. S. et al., Indian J. Anim. Sci., 42 (7): 520–525, Jul. 1972, Utilization of Manure in Poultry Feeds.

*Primary Examiner*—Shep K. Rose
*Attorney, Agent, or Firm*—Robert Shaw

[57] ABSTRACT

A mixture of avian intestinal microflora for administration to poultry to prevent or inhibit paratyphoid salmonella infection (including infection by the arizona groups) in the poultry or in the presence of infection to reduce the incidence and excretion rate of paratyphoid salmonella, is disclosed.

47 Claims, No Drawings

MIXTURE TO PROTECT POULTRY FROM SALMONELLA

The present invention relates to material which inhibits the implantation of salmonella in poultry and to the use of such materials to prevent such implantation in poultry.

BACKGROUND OF THE INVENTION

The fact that the intestinal microflora of salmonella-free birds inhibits the implantation of salmonella in other birds has been reported. Attention is called to a writing of the present inventors entitled "Protecting Chicks and Poults from Salmonella by oral Administration of 'Normal' gut Microflora" (Snoeyenbos et al) *Avian Diseases*, Vol. 22, No. 2, April–June, 1978, pp. 273–287; the writing and the references therein cited may be used as background for the present disclosure and is drawn upon hereinafter. This writing and the references cited therein are expressly incorporated herein by reference.

The effect of salmonella upon poultry (e.g. chicks and turkey poults) is three-fold; the salmonella acts to infect the poultry; it may be passed to human consumers of the poultry; and it appears in the excrement of the poultry. It is noted in said writing that the resistance of young chicks and turkey poults increased by early administration thereto of microflora in intestinal contents or feces from selected adult chickens. Since poultry forms an important food source, it is of the utmost importance that salmonella infection which endanger human health be eliminated from birds to be used as food. Consequently, poultry flocks which are found to have such infection in some birds are frequently entirely destroyed, at great economic hardship. There is an urgent need for a means of preventing or reducing to a minimum such infection of poultry flocks.

THE INVENTION

We have found that the administration to young poultry of salmonella implantation resistant avian intestinal microflora obtained from pathogen-free birds forms a safe and effective way to prevent or inhibit the chance of infestation of poultry flocks by paratyphoid salmonella and thus produces a healthy flock of birds capable of safe human consumption as food. We have found, further, that such microflora, in a lyophilized or other dried condition, forms a stable article which can be reconstituted by the poultry grower and so used.

Accordingly, it is an object of the present invention to provide a mixture of avian intestinal microflora which inhibits colonization of paratyphoid salmonella, including arizona groups, in chicks and turkey poults.

Another object is to provide a mixture that is free of known avian and/or human pathogens.

A further object is to provide a method of treating poultry with a mixture of gut microflora that maintains optimum biological protective effect throughout the life of the poultry.

A still further object is to provide a material and method of administering the same, for the protection of a living organism against a specific group of pathogens.

These and still further objects are addressed hereinafter.

DISCUSSION OF THE INVENTION

Some comments of a general nature are in order to provide a foundation for the more detailed discussion later. While the teachings herein are broader in scope, they are discussed in the context of inhibiting intestinal colonization by salmonella, including the arizona groups, in poultry and, more precisely, chicks and turkey poults (also called "treated birds" herein) by administering to the chicks and turkey poults a mixture of substantially pathogen-free avian intestinal microflora having the property of blocking subsequent colonization by paratyphoid salmonella, including the arizona groups, in the poultry in which the mixture is established. The term paratyphoid salmonella is used to cover the non host-adapted salmonella, and to exclude the host adapted *salmonella pullorum* and *salmonella gallinarum*. The dosage administered to the treated birds ideally is an amount which will result in substantially complete exclusion of salmonella from the intestines of the treated birds within about seventy-two hours. A larger dosage hastens the development of such exclusion, a smaller dosage delays the development of such exclusion. Later it is shown that a ½ ml. dosage of a 1–4 mixture of fecal material is more than adequate for present purposes.

The original source of microflora to be used in this invention is the fecal droppings of salmonella-free birds which have been tested and found by the known methods in the art to inhibit actively the implantation of salmonella in young chicks. This is then propagated and, at the same time, freed of pathogens by anaerobic culture (in which medium the microflora propagate but the pathogenic viruses do not, thus diluting the virus concentration to minimal).

The actual production of large quantities of the mixture to be administered, as a preventive measure, to young birds, is then effected by establishing this pathogen-free culture in substantially pathogen-free poultry (also called "pathogen-free poultry or birds" herein) within a short time (typically about twenty-four to seventy-two hours) of hatching of the poultry. The fecal droppings of the poultry are collected and the droppings are treated to prevent inactivation thereof. Typically, the treatment is that of lyophilizing the droppings, but they can be maintained at dry ice temperature or liquid nitrogen temperature to prevent inactivation. Also, typically, coarse particulate matter is separated from the droppings and the remainder is cultured anaerobically to increase the population of the active ingredients (i.e., microflora) thereof. It is, then, the cultured microflora that is lypholized or otherwise treated to prevent inactivation.

Terms used herein are employed in their accepted sense and/or are defined. In this connection, various avian pathogens are listed, among other placed, in the publication "Isolation and Identification of Avian Pathogens" published by the American Association of Avian Pathologists. Bergey's Manual of Determinative Bacteriology, 8th Ed. (Backman and Gibbons) Williams and Wilkins, Editors, Baltimore, Maryland, may be used. Reference is made below to pathogen-free (SPF) chicken breeding stock. Such breeding stock may be obtained from SPF type eggs from a number of sources; the eggs used were obtained from SPAFAS, Incorporated, R.F.D. No. 3, Norwich, Connecticut (hereinafter called SPAFAS). Other SPF type eggs and/or chicks are available from Larson Laboratory Eggs, Inc., 1412

Park Street, Box D, Gowrie, Iowa, Truslow Farms, Chester, Pa., and Lohman and Company, Cuxhaven, Germany. The egg groups available are SPF-utility, SPF-cofal and SPF-cofal/Marek; the negative tests applied to each egg group classification is published by the producer. As used herein, the term salmonella is used to denote salmonella groups including the arizona groups which are not host adapted. Especially important are the paratyphoid salmonella, including arizonas.

A culture of the avian microflora described above has been deposited with the American Type Culture Collection (ATCC 31413), and is available for the public in accordance with the provisions of MPEP 608.01(p).

Our invention can be further described and explained by the following examples:

EXAMPLE 1

Process to Secure an Effective Microflora in Pathogen-Free Birds from Donor Birds of Unknown Status Fresh fecal droppings were collected from donor birds known to have effective microflora and suspended in 4 parts of physiological saline to 1 part by weight of fecal droppings. After removing coarse particulate matter from the droppings by filtration through 4 layers of cheesecloth, 1 ml. portions of the filtrate were transferred to tubes containing 19 ml. of VL broth with 10% fecal extract and 5% liver extract as described by Barnes and Impey (Barnes, E. M., and C. S. Impey, 1970, British Poult. Sco., 11:467–481). The broth was incubated for 96 hours at 37° C. under anaerobic conditions to increase the population of microflora therein. Following incubation, 1 ml. of the broth mixture was removed, diluted with 4 ml. of VL broth and 1 ml. of that mixture was transferred to each of several tubes containing 19 ml. of sterile VL broth which was anaerobically incubated at 37° C. for an additional 96 hours. One additional transfer was made in the same manner which resulted in a $1 \times 10^6$ dilution of the original fecal sample. This serial method of anaerobic culture served to dilute viruses in the original inoculum to the point of extinction while maintaining the original bacterial flora. Following 96 hours of anaerobic incubation of these tubes at 37° C., 0.5 ml. of the cultured mixture was placed by pipette into the crop of each of 50 newly-hatched chicks, that is, chicks within 72 hours of hatching.

The above chicks were progeny of specific pathogen-free breeding stock (SPAFAS, SPF, Cofal/Marek) maintained under rigid isolation and periodically tested by appropriate methods to assure freedom from bacterial and viral pathogens as specified below for testing of these chicks.

Following administration of the VL broth culture, the chicks were placed in wire floored batteries in a room maintained under comprehensive isolation management.

All birds in the group were individually blood sampled at six weeks of age and each serum tested by appropriate serologic tests to assure freedom from antibodies to the following avian pathogens:

Adenoviruses (11 types)
Fowl Pox
Infectious Bronchitis
Infectious Bursal Agent
Infectious Laryngotracheitis
Influenza (Type A)
Lymphoid Leukosis
Marek's Disease
Mycoplasma Gallisepticum
Mycoplasma Synoviae
Newcastle Disease
Reovirus, Avian
Reticuloendotheliosis
Avian Encephalomyelitis
Salmonella Pullorum-typhoid
Egg-drop Adeno-line Virus Additionally, all birds were determined to be free of non host-adapted salmonella, including arizona groups, by periodic selective enrichment culture of fecal droppings and by similar culture of individual birds.

The entire group of birds was tested at two additional monthly intervals after six weeks by all the above methods. Samples of fecal droppings were collected between the six and ten week test periods for lyophilization or preservation for "seed" inoculum.

Also samples of feces from the group of birds were examined at weekly intervals starting at four weeks of age to assure absence of coccidia and ova of nematodes, trematodes and cestodes. This examination was by standard sugar flotation methods. No special effort was made to detect the possible presence of flagellated protozoa as this group of organisms is unable to withstand lyophilization.

EXAMPLE 2

Methods for Determining Effectiveness of Microflora in Preventing Salmonella Colonization by Competitive Exclusion in Treated Birds In both Method A and Method B described below it is necessary to use chicks or turkey poults that are known to be free of all salmonella, including the arizona groups. Either Method A or Method B may be used for evaluation.

Method A

Each test requires at least one group of 10 one-day-old chicks or turkey poults which are pretreated by administering into the crop by a pipette a standard amount of the selected microflora (usually in 0.5 ml. quantity). The chicks are then placed in a clean starting battery on a new litter in a clean pen and fed and watered. A comparable group not pretreated with microflora is similarly placed in a separate clean room as controls.

After twenty-four hours, chicks (or poults) of the same age are infected with salmonella by administering into the crop approximately $1 \times 10^5$ viable cells from a twenty-four hour broth culture of the test paratyphoid salmonella (either *S. typhimurium*, *S. infantis*, or *S. enteritidis*). Pathogenic strains are used. Two infected birds are added to each test group as "seeder" birds.

All birds in each test group are then individually cultured by cloacal swab at one, two and three weeks of age. Effective protection by microflora used for the original pretreatment is indicated by few or no isolations of salmonella from the pretreated birds and isolation of salmonella from all or substantially all of the control group and from the "seeder" birds.

Method B

This test method is started as described under Method A except that the test birds are placed in wire floored starting batteries.

No seeder chicks are introduced, and inserted at seventy-two hours all birds are individually dosed by administering into the crop approximately $1 \times 10^5$ viable cells of the test salmonella previously described under Method A. As this severe challenge may result in pretreated birds shedding salmonella, measurements are made by counting by standard methods viable salmonella in mixed fecal droppings collected from each group of birds. (Use of naladixic acid resistant strains of salmonella for challenge facilitates enumeration.)

The control group that has not been pretreated excrete very large numbers of viable salmonella ($1 \times 10^4 \rightarrow 1 \times 10^7$ or more) cells per gram of wet feces. The pretreated group excrete very few if any viable salmonella (usually less than $1 \times 10^2$) cells per gram of wet feces. Counts are made at three and seven days after challenge.

The avian microflora of the present invention may be established in the gastrointestinal tract of the poultry, for example, by introducing or administering it in water fed to the poultry, internasally as an aerosol or it may be added to feed with precaution against infection. Proper treatment of the newly-hatched birds serves to inhibit the subsequent colonization of the intestinal tract thereof by salmonella, nevertheless, this is as inhibition only and this can be overcome by severe exposure. The avian microflora so administered, it is believed, functions by way of competitive exclusion. It should be noted, also, that the material so administered may also play a role in protecting birds against other enteric infections.

The SPAFAS, SPF-Cofal/Marek flock above mentioned is checked for freedom from the following avian pathogens:

Adenoviruses, Avian
    Fowl Pox
    Infectious Bronchitis
    Infectious Bursal Agent
    Infectious Laryngotracheitis
    Influenza (Type A)
    Lymphoid Leukosis Viruses
    Lymphoid Leukosis Antibody
    Lymphoid Leukosis Antibody
    Marek's Disease
    Mycoplasma Gallisepticum
    Mycoplasma Synoviae
    Newcastle Disease
    Reoviruses, Avian
    Reticuloendotheliosis
    Salmonella Pullorum-typhoid
    Avian Encephalomyelitis
    Haemophilus Gallinarum The term microflora is used above to denote living organisms present in the fecal droppings of poultry. Pathogen-free or substantially pathogen-free avian intestinal microflora means microflora that has an indiscernible amount of pathogens therein, or, at least, an amount that is below a level that will affect birds if introduced thereto in the manner described herein.

Modifications of the invention herein disclosed will occur to persons skilled in the art.

What is claimed is:

1. A mixture of avian intestinal microflora treated to prevent inactivation thereof,
    said microflora having the property of blocking subsequent colonization in the intestinal tract of poultry by paratyphoid salmonella,
    said mixture being substantially free of pathogens.

2. A mixture as claimed in claim 1 wherein the avian intestinal microflora is lyophilized to prevent inactivation thereof.

3. For administering to poultry, a mixture of avian intestinal microflora treated to prevent in activation thereof, said microflora having the property of blocking the subsequent colonization in the intestinal tract of treated poultry by salmonella, said mixture being substantially free of the following pathogens:
    Adenoviruses (11 types)
    Fowl Pox
    Infectious Bronchitis
    Infectious Bursal Agent
    Infectious Laryngotracheitis
    Influenza (Type A)
    Lymphoid Leukosis
    Marek's Disease
    Mycoplasma Gallisepticum
    Mycoplasma Synoviae
    Newcastle Disease
    Reovirus, Avian
    Reticuloendotheliosis
    Avian Encephalomyelitis
    Salmonella Pullorum-typhoid
    Egg-drop Adeno-like Virus.

4. For administering to poultry, a mixture of poultry intestinal microflora treated to prevent inactivation thereof, said microflora having the property of blocking the subsequent colonization in the intestinal tract of the treated poultry by paratyphoid salmonella, said mixture being free of the following pathogens:
    Adenoviruses, Avian
    Fowl Pox
    Infectious Bronchitis
    Infectious Bursal Agent
    Infectious Laryngotracheitis
    Influenza (Type A)
    Lymphoid Leukosis Viruses
    Lymphoid Leukosis Antibody
    Lymphoid Leikosis Antibody
    Marek's Diease
    Mycoplasma Gallisepticum
    Mycoplasma Synoviae
    Newcastle Disease
    Reoviruses, Avian
    Reticuloendotheliosis
    Salmonella Pullorum-typhoid
    Avian Encephalomyelitis
    Haemophilus Gallinarum.

5. A process for producing a mixture of substantially pathogen-free avian intestinal microflora having the property of blocking subsequent colonization by paratyphoid salmonella in poultry in which it is established, which comprises transferring starting avian microflora known to be capable of said blocking of subsequent colonization to newly-hatched pathogen-free poultry, recovering said microflora from the fecal droppings of said poultry in a manner precluding subsequent contamination by pathogens, and subsequently recovering said pathogen-free microflora from the fecal droppings of said poultry.

6. The process of claim 5 in which the newly-hatched pathogen-free poultry is less than about seventy-two hours old.

7. The process of claim 6 in which the pathogen-free microflora are cultured to increase the population thereof.

8. The process of claim 7 in which cultured pathogen-free microflora are treated to prevent inactivation thereof.

9. The process of claim 8 in which the treatment of the cultured pathogen-free microflora to prevent inactivation is by lyophilization.

10. The process of claim 8 in which said treatment comprises maintaining the cultured pathogen-free microflora at liquid nitrogen temperature.

11. The process of claim 8 in which said treatment comprises maintaining the cultured pathogen-free microflora at the temperature of dry ice.

12. A process for producing a mixture of substantially pathogen-free avian intestinal microflora having the property of blocking subsequent colonization by salmonella in the intestinal tracts of poultry in which it is established which comprises the steps of
   a. establishing avian microflora, known to be capable of said blocking of subsequent colonization, in substantially pathogen-free poultry within about seventy-two hours of hatching of said poultry;
   b. collecting the fecal droppings of said poultry;
   c. separating any particulate matter from said droppings from the remainder;
   d. culturing the remainder of said droppings anaerobically to increase the population of microflora therein, and
   e. lyophilizing the cultured microflora.

13. The process of claim 12 in which the said poultry are chickens.

14. The process of claim 12 in which the said poultry are turkeys.

15. A method of inhibiting the infection of a flock of poultry by non host-adapted salmonella which comprises administering to poultry no more than about seventy-two hours old an effective amount of avian intestinal microflora,
   said microflora having the property of blocking subsequent colonization in the intestinal tract of poultry by paratyphoid salmonella;
   said microflora being substantially free of avian pathogens.

16. The method of claim 15 in which the poultry are chickens hatched and raised in an environment separated from adult birds.

17. The method of claim 15 in which the poultry are turkeys hatched and raised in an environment separated from adult birds.

18. The method of claim 15 wherein the micro flora are administered directly to the crop of the poultry.

19. The method of claim 15 wherein the microflora are introduced to the drinking water of the microflora 20. A mixture of substantially pathogen-free avian intestinal microflora having the property of blocking subsequent colonization by salmonella in the intestinal tracts of poultry in which the intestinal microflora are established, prepared by a process which comprises transferring starting avian microflora known to be capable of said blocking of subsequent colonization to less than about seventy-two hour-old pathogen-free poultry by a method precluding simultaneous transfer of pathogens to said poultry, recovering the fecal droppings of said poultry in a manner precluding subsequent contamination by pathogens, and subsequently recovering pathogen-free microflora from the fecal droppings of said poultry.

21. The mixture of claim 20 in which the pathogen-free microflora from the fecal droppings is cultured to increase the population thereof.

22. The mixture of claim 21 in which the cultured pathogen-free microflora are subjected to lyophilization.

23. A lyophilized mixture of substantially pathogen-free avian intestinal microflora having the property of blocking subsequent colonization by salmonella in the intestinal tracts of poultry in which the microflora are established, prepared by a process which comprises a process for producing a mixture of substantially pathogen-free avian intestinal microflora having the property of blocking subsequent colonization by salmonella in the intestinal tracts of poultry in which the microflora are established which comprises the steps of
   a. introduction of avian microflora, known to be capable of said blocking of subsequent colonization, in substantially pathogen-free poultry within about seventy-two hours of hatching of said poultry;
   b. collecting the fecal droppings of said poultry; and
   c. lyophilizing said droppings to prevent inactivation of the microflora therein.

24. A process for producing substantially pathogen-free microflora having the property of inhibiting subsequent colonization by salmonella in the intestinal tracts of poultry in which the microflora are established which comprises: introduction of microflora, known to be capable of said inhibiting of subsequent colonization, in substantially pathogen-free poultry within a short time of hatching of said poultry; collecting the fecal droppings of said poultry, which fecal droppings contain said pathogen-free microflora; and treating said droppings to prevent inactivation of the microflora therein.

25. A mixture of avian intestinal microflora treated to prevent inactivation thereof,
   said microflora having the property of blocking subsequent colonization in the intestinal tract of poultry by paratyphoid salmonella,
   said mixture being substantially free of pathogens that infect poultry.

26. A mixture as claimed in claim 25 wherein the avian intestinal microflora is lyophilized.

27. A process for producing a mixture poultry intestinal microflora having the property of blocking subsequent colonization by paratyphoid salmonella in poultry in which it is established, which comprises transferring starting poultry microflora known to be capable of said blocking of subsequent colonization to seeder poultry free of pathogens that infect poultry, said starting microflora being substantially free of pathogens that infect poultry, recovering said poultry intestinal microflora from the fecal droppings of said seeder poultry in a manner precluding subsequent contamination by pathogens that infect poultry.

28. A process for producing microflora substantially free of avian pathogens and having the property of inhibiting subsequent colonization by salmonella in the intestinal tracts of poultry in which the microflora are established which comprises: introduction of microflora, known to be capable of said inhibiting of subsequent colonization, in poultry substantially free of avian pathogens; collecting the fecal droppings of said poultry, which fecal droppings contain said microflora substantially free of avain pathogens; and treating said droppings to prevent inactivation of the microflora therein.

29. A mixture of poultry intestinal microflora substantially free of pathogens that infect poultry and having the property of blocking subsequent colonization by salmonella in the intestinal tracts of poultry in which the intestinal microflora are established, prepared by a process which comprises transferring starting poultry microflora known to be capable of said blocking of subsequent colonization to poultry, substantially free of pathogens that infect poultry, by a method precluding simultaneous transfer of pathogens thereto, recovering the fecal droppings of the poultry in a manner precluding subsequent contamination by pathogens that infect poultry, and subsequently recovering microflora substantially free of pathogens that infect poultry from the fecal droppings of the poultry.

30. A method of inhibiting the infection of poultry by non-host-adapted salmonella which comprises administering to the poultry an effective amount of poultry intestinal microflora, said microflora having the property of blocking subsequent colonization in the intestinal tract of poultry by salmonella, said microflora being substantially free of pathogens that infect poultry.

31. The method of claim 30 in which the poultry are chickens.

32. The method of claim 30 in which the poultry are turkeys.

33. A method of affecting the infection of poultry, which poultry is brooded and reared separate from adult birds, by salmonella which comprises administering to the poultry an effective amount of poultry intestinal microflora, said microflora hiving the property of blocking subsequent colonization in the intestinal tract of poultry by salmonella, said microflora being substantially free of pathogens that infect poultry.

34. A mixture of avain intestinal microflora substantially free of poultry pathogens and having the property of blocking subsequent colonization by salmonella in the intestinal tracts of poultry in which the poultry intestinal microflora are established, prepared by a process which comprises transferring starting avian microflora known to be capable of said blocking of subsequent colonization to seeder birds, substantially free of poultry pathogens, by a method precluding simultaneous transfer of poultry pathogens thereto, recovering the fecal droppings of the seeder birds in a manner precluding subsequent contamination by poultry pathogens, and subsequently recovering microflora substantially free of pathogens that infect poultry from the fecal droppings of the seeder birds.

35. A process as claimed in claim 5 in which the effectiveness of the substantially pathogen-free microflora in blocking subsequent colonization by paratyphoid salmonella in treated poultry is determined in accordance with EXAMPLE 2 herein.

36. A process as claimed in claim 5 in which the effectiveness of the substantially pathogen-free microflora in blocking subsequent colonization by paratyphoid salmonella in treated poultry is determined in accordance with a test procedure based on the teachings disclosed herein.

37. A mixture of poultry intestinal microflora collected from the fecal droppings of specific pathogen-free poultry, chicks and poults, progeny of specific salmonella and other pathogen-free chicken and turkey breeding stock maintained under rigid isolation and periodically tested to assure freedom from salmonella and all other specific bacterial and viral pathogens, in which pathogen-free cultures have been established within about twenty-four to seventy-two hours of hatching of the poultry, said droppings having had coarse particulate matter separated therefrom and the remainder cultured anaerobically to increase to population of the active microflora therein and having been treated to prevent inactivation thereof by lyophilizing the microflora or by maintaining the microflora at dry ice temperature or at liquid nitrogen temperature, said microflora having the property of blocking subsequent coloinzation in the intestinal tract of poultry by paratyphoid salmonella, said mixture being substantially free of pathogens.

38. A mixture as claimed in claim 3 wherein said avian intestinal microflora are poultry microflora collected from the fecal droppings of specific pathogen-free poultry, chickens and trukeys, progeny of specific chicken and poultry breeding stock substantially free of said pathogens.

39. A mixture as claimed in claim 38 in which said fecal droppings have had coarse particulate matter separated therefrom and the remainder cultured anaerobically to increase the population of the active microflora therein 40. A mixture as claimed in claim 3 wherein said mixture is dried by lyophilizing or maintained at dry ice temperature or maintained at liquid nitrogen temperature to prevent inactivation thereof.

41. A mixture as claimed in claim 4 wherein said avian intestinal microflora are poultry microflora collected from the fecal droppings of specific pathogen-free poultry, chickens and turkeys, progeny of specific chicken and poultry breeding stock free of said pathogens.

42. A mixture as claimed in claim 41 in which said fecal droppings are substantially free of coarse particulate matter and in which the fecal droppings have been cultured to increase the population of the active microflora therein.

43. A mixture as claimed in claim 4 wherein said mixture is dried by lyophilizing or maintained at dry ice temperature or maintained at liquid nitrogen temperature to prevent inactivation thereof.

44. A process as claimed in claim 27 wherein said poultry are chickens, wherein said seeder poultry are progeny of substantially pathogen-free chickens, wherein the droppings are cultured to increase the population of the microflora therein while diluting any said pathogens therein.

45. A process as claimed in claim 44 in which the droppings are cultured by a serial method that comprises a plurality of serial anaerobic culturing steps and in which the resultant product, after culturing, is treated to prevent inactivation of the microflora therein.

46. A process as claimed in claim 27 wherein said poultry are turkeys, wherein said seeder poultry are progeny of substantially pathogen-free turkeys, wherein the droppings are cultured to increase the population of the microflora therein while diluting any said pathogens therein.

47. A process as claimed in claim 46 in which the droppings are cultured by a serial process that comprises a plurality of serial anaerobic culturing steps to produce said mixture and in which the resultant mixture after culturing is treated to prevent inactivation of the microflora therein.

* * * * *